United States Patent
Abrams et al.

Patent Number: 5,813,970
Date of Patent: Sep. 29, 1998

[54] MEDICAL MAGNETOICTAL THERAPY

[75] Inventors: Richard S. Abrams, Vernon Hills, Ill.; Conrad M. Swartz, Greenville, N.C.

[73] Assignee: Somatics, Inc., Lake Bluff, Ill.

[21] Appl. No.: 231,307

[22] Filed: Apr. 22, 1994

Related U.S. Application Data

[63] Continuation-in-part of Ser. No. 986,429, Dec. 4, 1992, abandoned.

[51] Int. Cl.$^6$ .................................................. A61N 1/00
[52] U.S. Cl. ........................................ 600/14; 128/898
[58] Field of Search ................... 600/9–15; 128/897–98; 607/45

[56] References Cited

PUBLICATIONS

Mansfield et al, "NMR Imaging in Biomedicine", Apr. 13, 1982, pp. 297–332.

*Primary Examiner*—John P. Lacyk
*Attorney, Agent, or Firm*—Eliot S. Gerber

[57] ABSTRACT

A magnetic induction coil is placed next to the scalp of a patient. A pulse train of high energy electrical waves is flowed through the induction coil to produce a sufficiently strong magnetic field to generate currents in the patient's brain for the therapy of neurologic or psychiatric illnesses. These currents induced in the brain cause multifocal neuronal discharge to induce a generalized convulsive neuronal discharge.

6 Claims, 2 Drawing Sheets

MEDICAL MAGNETOICTAL THERAPY

CROSS REFERENCE TO OTHER APPLICATION

This application is a continuation-in-part application partly based on application Ser. No. 07/986,429, filed Dec. 4, 1992, and now abandoned.

FIELD OF THE INVENTION

The present invention relates to medical methods and more particularly to a method of generating electrical currents inside the brain of a human patient for the purpose of inducing brain seizures to treat certain neurologic and psychiatric disorders.

DESCRIPTION OF THE RELATED ART

The related art discloses various methods used in the past for inducing brain seizures in patients for the treatment of certain neurologic and psychiatric disorders ("neuropsychiatric disorders"), particularly certain types of depression. For example, brain seizures may be induced in human patients by the injection of chemical convulsant agents (pentylenetetiazol), the inhalation of gaseous convulsant agents (e.g. flurothyl, Regan U.S. Pat. No. 3,976,788), or by the application of electric currents to the scalp in a procedure termed electroconvulsive therapy (ECT), sometimes referred to as "shock therapy". Only ECT is still used to induce therapeutic brain seizures.

In addition, nonconvulsive electrical stimulation therapy (NCEST) methods are known in which low-energy currents are applied to the heads of human patients to stimulate brain responses without inducing seizures.

In a present method of ECT, a pulsed or sinusoidal current of constant amperage or constant voltage is applied through electrodes to the patient's head for a period of 1–10 seconds. There are various possible drawbacks to ECT, however. These drawbacks include:

1) The electrical resistance of the skull to the passage of current greatly attenuates the amount of current that actually reaches the brain. The rest of the current is shunted through the skin and scalp. Increasing the amount of current applied to the head, to reach the minimum required to induce seizures, may result in burns to the scalp and skin from the shunted current.

2) Because the direct passage of electric current through the relatively high-impedance skin during ECT can cause skin burns, the doctor must reduce the impedance of the electrode-to-skin interface by first cleansing the skin, then wiping the skin dry, and applying conductive gel over the metal electrode surfaces and their application sites on the skin. Special effort is then required of the doctor to ensure that the metal disc electrodes are applied firmly to the skin, either by holding them in place with a rubber headstrap, or holding them with manually-applied nonconductive electrode handles. Alternatively, self-adherent, solid-gel disposable stimulus electrodes can be used, after first cleansing the skin and then wiping the skin dry. Metal disc electrodes, rubber headstraps, nonconductive electrode handles, and disposable self-adherent stimulus electrodes are all costly to purchase and time-consuming to maintain and use.

3) The attenuated current that finally penetrates the skull is often capable only of stimulating seizures over the surface (cortex) of the brain. These seizures must then spread by secondary means to the deeper brain structures where the therapeutic effects of a seizure are believed to occur. Often these secondary means of spread are insufficient to induce therapeutic remission of the disorder.

4) It has been reported that memory loss may accompany the passage of current through the temporal lobes of the brain.

5) Leakage currents from defective equipment may reach the patient through the electrodes. Such leakage currents are dangerous to patients with cardiac arrhythmias or pacemakers. This requires that the ECT equipment undergo regular, and expensive, calibration checks.

6) The negative stigma to much of the public to the phrase "shock therapy" causes many patients to refuse the treatment even though it would be beneficial to them.

7) All convulsive therapies, including ECT, induce generalized brain seizures that stimulate superficial and deep subcortical brain structures indiscriminately. In some neuropsychiatric disorders, however, it is only the deep brain structures (e.g. the diencephalon) that functions abnormally and therefore requires stimulation.

8) Generalized seizures have hemodynamic consequences (hypertension, tachycardia, increased intracanial pressure) that can present unacceptable risks to patients with pre-existing cerebral, cardiovascular, or cerebrovascular conditions (e.g. myocardial infarction, hypertension, stroke, brain tumor). These result from the spread of seizure activity into brain areas that control cardiovascular excitation, such as the medulla.

BRIEF SUMMARY OF THE INVENTION

The present invention comprises a method for stimulating surface, intermediate, or deep brain structures by the application of pulsed magnetic fields near the outside surface of the patient's head. The generated magnetic fields induce corresponding electrical fields in surface and deep brain structures, thereby depolarizing nerve cells and raising their level of excitation closer to the point of neuronal discharge.

In the present embodiment, designated magnetoconvulsive therapy (MCT), electrical fields of amplitude sufficient to cause neuronal discharge are induced in the brain by the generated magnetic fields, intended to induce a generalized therapeutic brain seizure. In another embodiment, limited magnetoictal therapy (LMIT), seizure is restricted to one or more circumscribed brain volumes by focusing the applied magnetic fields and their changes within the perimeters of such volumes and limiting the number of sites of neuronal discharge so as to avoid substantial spread of seizure activity outside the volume. This second strategy might be aided by pretreatment of the patient with one or more anticonvulsant pharmaceutical agents to limit the spread of seizure activity.

In the method of the present invention a storage capacitor is discharged into a stimulating coil by means of one or more solid-state switches. The coil is positioned next to the head of the patient. The current in the coil generates a magnetic field pulse that induces a secondary current in the brain tissue. This secondary current may be focused on a specific region in the brain by selectively manipulating the position of the coil three dimensionally around the patient's head.

The voltage waveshape of the secondary current induced in the brain tissue is proportional to the rate of change of the magnetic field pulse. For MCT and LMIT the primary coil current is in the range of 5,000 to 30,000 amps (A) and is preferably 10,000 A to 20,000 A and the power is in the preferred range of 1500–3000 watts. The delivered pulse, for example, may be a single monophasic sine or cosine pulse with a duration of 100 to 300 microseconds (usec) or, alternatively biphasic pulses of the same duration. The pulse repetition rate is 5 to 90 Hz. The pulse train is applied for about 0.1 to 60 seconds, preferably for about 10–20 seconds. The preferred stimulus for magnetoconvulsive therapy (MCT) is a 10 to 20 second pulse train at a frequency of 25 to 50 Hz. The magnetic field produced by the magnetic induction coil is at least 0.1 Tesla and is preferably in the range of 0.5 to 2 Tesla.

The several advantages of the method of the present invention are as follows.

1. Because the present method does not apply electric currents to the skin; it does not expose the subject to the risk of skin burns.
2. Because the magnetic fields require no direct contact with the skin, time-consuming skin preparation is unnecessary and no costly stimulus electrodes or accessories are required.
3. Because the bony skull does not significantly impede the transmission of magnetic fields, there is no attenuation of the therapeutic stimulus before it reaches the deep brain structures: the intended strength electrical field current is directly induced in the brain region specified with MCT.
4. Because magnetic fields can be oriented in three dimensions, to induce focused electrical field currents in deep brain structures, there is no necessity for the spread, and consequent attenuation, of brain tissue excitation from superficial to deep structures during the application of such magnetic fields.
5. Because the invented method does not pass external electric currents through the temporal lobes, its use in MCT would not cause the same deleterious memory effects that have been reported in some cases from ECT.
6. Because the present method does not apply electric currents to the skin, the patient receiving MCT does not experience the painful electrical sensations or shocks possible with ECT.
7. Because the invented method requires no patient electrical or mechanical contact, the patient receiving MCT is not subjected to the risks of leakage currents, thereby eliminating the need for costly and time-consuming leakage current tests of the device.
8. Because no electrical stimuli or shocks are applied to the subject's head, the method of MCT cannot accurately be labeled as "shock therapy", thus avoiding the prejudicial implications, to some members of the public, of this term.

DETAILED DESCRIPTION OF THE INVENTION

Figure 1:
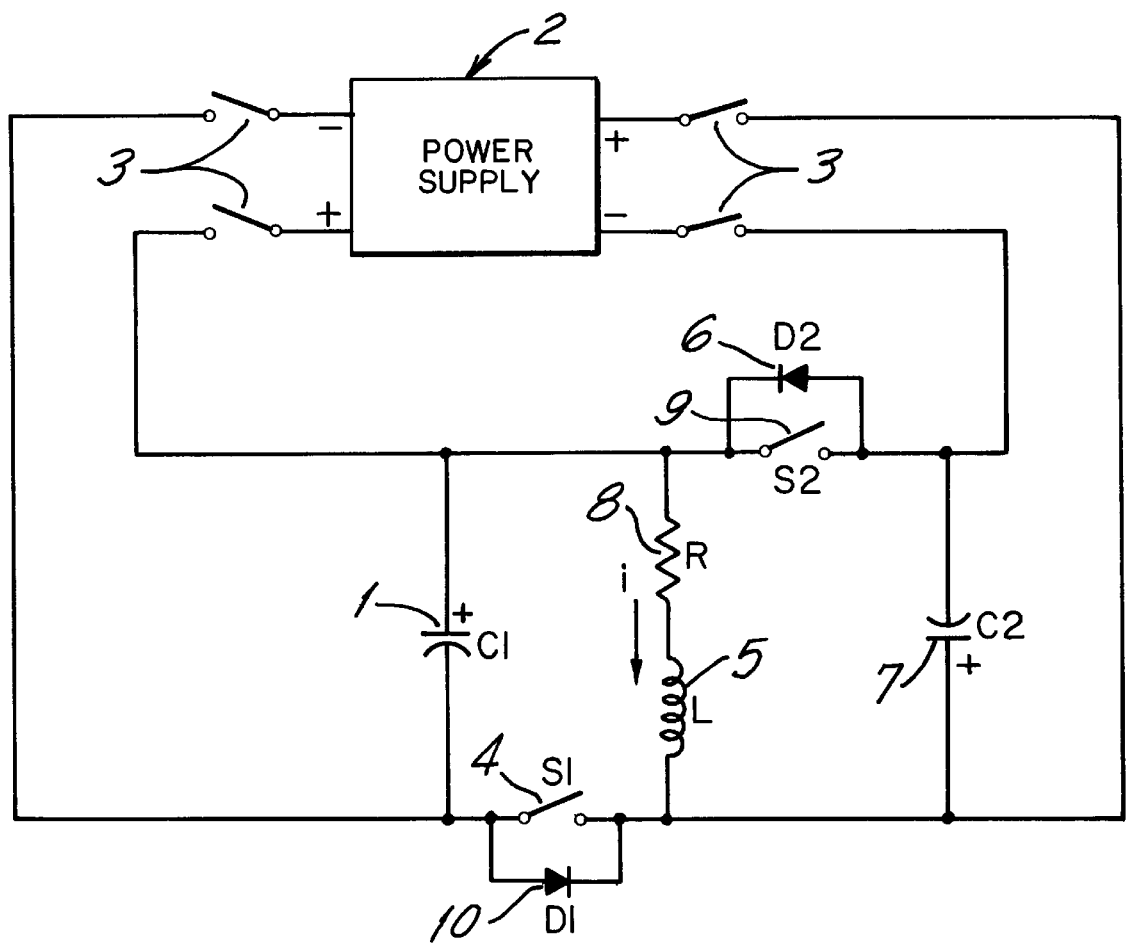
FIG. 1 is a circuit diagram of a magnetic stimulator.

The magnetic stimulator circuit of FIG. 1 is suitable for a device to induce sufficient electrical currents in the living tissue of the brain of a human patient to induce brain seizure and thereby treat neuropsychiatric disorders. Capacitor 1 (C1) is initially charged by a power supply 2 that is connected to capacitor 1 (C1) by solid state switches 3. When capacitor 1 (C1) reaches a sufficient charge, these switches 3 open and the power supply 1 is disconnected from the circuit. Switch 4 (S1) is then closed, completing a circuit loop containing capacitor 1 (C1) switch 4 (S1), inductor coil 5 (L) and resistor 8 (R). Resistor 8 (R) represents the combined resistance of the cables, switches, capacitors, and coil L, and ideally is very low. The closing of switch 4 (S1) allows the charge on capacitor 1 (C1) to be discharged through the coil 5 (L). The current, i, in the coil 5 reaches its maximum when the voltage on capacitor 1 (C1) reaches zero. At that moment, switch 4 (S1) is opened and the inductive force of coil 5 (L) turns on diode 6 (D2) and charges capacitor 7 (C2). Most of the initial charge on capacitor 1 (C1) will thus be transferred to capacitor 7 (C2) with relatively small losses due to the stimulation pulse. The power supply used to charge capacitor 1 (C1) is also switchable and is connected to capacitor 7 (C2) to "top off" capacitor 7 (C2). When capacitor 7 (C2) is fully charged, switch 9 (S2) closes and capacitor 7 (C2) discharges through the coil 5 (L) opening switch 9 (S2). When the voltage on capacitor 7 (C2) reaches zero inductor coil 5 (L) turns on diode 10 (D1) to "recharge" capacitor 1 (C1) and capacitor 7 (C2). The use of the inductive coil 5 (L) to recharge each capacitor 1 (C1) and 7 (C2) allows the capacitors to be recharged faster than using the power supply by itself. This allows for a higher pulse repetition rate. Having the coil 5 (L) discharge its inductive energy by charging the capacitor 1 (C1) and 7 (C2), whenever switches 4 (S1) and 9 (S2) are opened, avoids having the coil 5 (L) dissipate that inductive energy as heat. This allows the device to have low heat dissipation and requires little, if any, external cooling.

Figure 2:
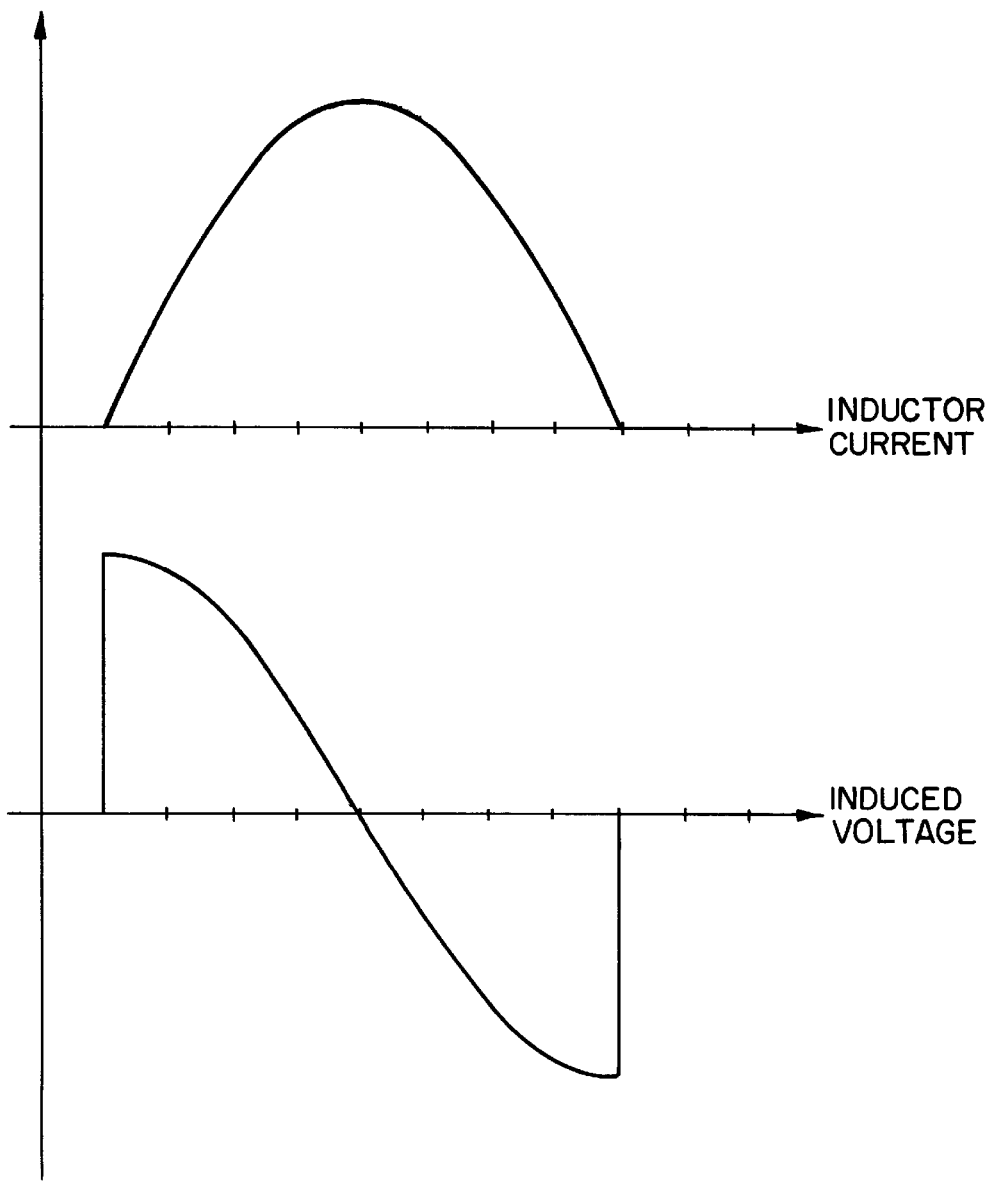
FIG. 2 illustrates the waveform of the current in the coil and the waveform of the voltage induced in the brain tissue.

The inductor current, shown in FIG. 2, is proportional to the magnetic field induced by the coil 5 (L). This magnetic field generates an induced voltage in the brain tissue (also shown in FIG. 2) that is proportional to the rate of change (i.e., the first derivative) of the magnetic field. This results in the single monophasic cosine induced voltage pulse of FIG. 2.

One method of the present invention applies the induced voltage pulses to selected focus points within the brain. By proper selection of pulse repetition rate, amplitude and duration, therapeutic results in the treatment of neuropsychiatric disorders may be achieved. In magnetoconvulsive therapy (MCT), high energy electrical fields are generated in the brain at selected foci to induce therapeutic brain seizures.

The strength of the magnetic field flux created by the coil 5 (L) will vary from 0.1 to 2 Teslas. For magnetic fluxes above 0.5 Teslas it may be necessary and more practical to use super-conducting magnets to minimize size of the coil and power requirements. The superconductor magnet may be of the type used in magnetic resonance imaging (MRI) systems in which a liquid helium cryostat is used to refrigerate a Low-Te superconductive magnet.

Figure 3:
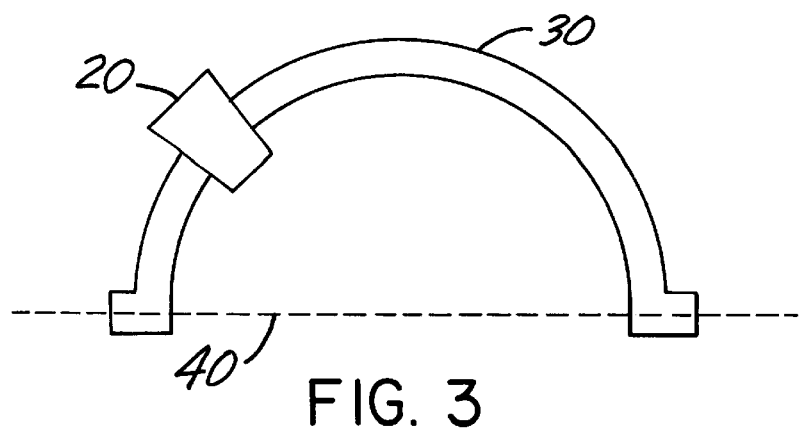
FIG. 3 is a top plan view of a magnetic stimulator system.

As shown in FIG. 3, the magnetic stimulation device may be housed in a Dewar container 20 that moves around the head on a semicircular track 30. The semicircular track 30 can then be pivotally mounted to allow the track to rotate about an imaginary axis 40 around the patient's head. This three dimensional positioning of the coil and the variance of the strength of the induced voltage allow the operator to induce a seizure at a particular focal point within the brain.

A suitable magnetic stimulus for magnetoconvulsive therapy (MCT) would be produced by an electric wave in the magnetic induction coil in the range of 5000 A to 30,000 A and preferably 10,000 A to 20,000 A; power of preferably 1500–3000 watts; a pulse duration in the range of 100 to 300 microseconds, preferably about 200 microseconds; a pulse rate of 5 Hz to 90 Hz, preferably 25 Hz to 50 Hz; and a pulse train duration in the range of 0.1 to 60 seconds, preferably about 10 to 20 seconds.

What is claimed is:

1. A method in medicine to purposefully induce a convulsive brain seizure in a human patient by a magnetic field to treat the patient's neuropsychiatric disorder, comprising:

positioning a magnetic induction coil proximate the head of the patient; and flowing a pulse train of electrical waveforms through the coil to produce a magnetic field to generate an electrical stimulus in the patient's brain to induce seizure.

2. A method in medicine as in claim 1 wherein the pulse train consists of a series of waves and is greater than 5000 amps in electrical current, the pulse train is in the range of 10–20 seconds in duration, each wave is less than 1 millisecond in duration, and the magnetic field produced thereby is at least 0.1 Tesla.

3. A method as in claim 1 wherein the magnetic induction coil is a superconductive coil cooled below its critical temperature.

4. A method as in claim 1 wherein the pulse train is 10–20 seconds in duration and at a frequency of 25–50 Hz.

5. A method as in claim 1 wherein the pulses have a pulse duration in the range of 100 to 300 microseconds, whether constant or varying systematically or nonsystematically within said range.

6. A method as in claim 1 wherein the seizure is a generalized convulsive neuronal discharge.

* * * * *